(12) United States Patent
Hildeberg et al.

(10) Patent No.: US 7,806,884 B2
(45) Date of Patent: Oct. 5, 2010

(54) ABSORBENT ARTICLE COMPRISING AN ELASTIC LAMINATE

(75) Inventors: Jenny Hildeberg, Landvetter (SE); Elisabeth Lakso, Stenungsund (SE)

(73) Assignee: SCA Hygiene Products AB, Gothenburg (SE)

(*) Notice: Subject to any disclaimer, the term of this patent is extended or adjusted under 35 U.S.C. 154(b) by 811 days.

(21) Appl. No.: 11/630,371

(22) PCT Filed: Jun. 22, 2004

(86) PCT No.: PCT/SE2004/001005

§ 371 (c)(1),
(2), (4) Date: Dec. 21, 2006

(87) PCT Pub. No.: WO2005/122985

PCT Pub. Date: Dec. 29, 2005

(65) Prior Publication Data

US 2007/0233034 A1    Oct. 4, 2007

(51) Int. Cl.
*A61F 13/15* (2006.01)
(52) U.S. Cl. .................. 604/385.27; 604/385.01; 604/385.22; 604/384; 604/378; 604/366; 604/385.31
(58) Field of Classification Search ........... 604/385.27, 604/366, 378, 384, 385.01, 385.22, 385.31
See application file for complete search history.

(56) References Cited

U.S. PATENT DOCUMENTS

| | | | |
|---|---|---|---|
| 4,119,450 A | 10/1978 | Bianco | |
| 4,663,220 A * | 5/1987 | Wisneski et al. | 428/221 |
| 4,698,261 A | 10/1987 | Bothe et al. | |
| 4,777,080 A | 10/1988 | Harris, Jr. et al. | |
| 4,842,596 A | 6/1989 | Kielpikowski et al. | |
| 4,932,949 A | 6/1990 | Thygesen et al. | |
| 5,114,781 A * | 5/1992 | Morman | 428/198 |
| 5,143,679 A | 9/1992 | Weber et al. | |
| 5,156,793 A | 10/1992 | Buell et al. | |

(Continued)

FOREIGN PATENT DOCUMENTS

EP    0 287 388    10/1988

(Continued)

OTHER PUBLICATIONS

International Search Report dated Feb. 10, 2005.

(Continued)

*Primary Examiner*—Jacqueline F. Stephens
(74) *Attorney, Agent, or Firm*—Buchanan Ingersoll & Rooney PC

(57) ABSTRACT

A pant type absorbent article such as a pant diaper, a sanitary pant or incontinence pant, the article having a core region including an absorbent core and a chassis region surrounding the core region. The article, at least in part of the chassis region, has a outer coversheet in the form of an elastic laminate having puncture resistance of at least 15N, wherein the laminate includes first and second layers of fibrous material and an elastic film layer located between the first and second fibrous layers and in which at least one of the layers of fibrous material has an elongation at maximum load greater than the elasticity of the elastic laminate.

24 Claims, 4 Drawing Sheets

U.S. PATENT DOCUMENTS

| | | | |
|---|---|---|---|
| 5,167,897 | A | 12/1992 | Weber et al. |
| 5,261,899 | A | 11/1993 | Visscher et al. |
| 5,336,545 | A | 8/1994 | Morman |
| 5,422,172 | A | 6/1995 | Wu |
| 5,462,541 | A | 10/1995 | Bruemmer et al. |
| 5,514,470 | A * | 5/1996 | Haffner et al. ............... 428/343 |
| 5,592,690 | A | 1/1997 | Wu |
| 5,634,216 | A | 6/1997 | Wu |
| 5,635,290 | A | 6/1997 | Stopper et al. |
| 5,706,524 | A | 1/1998 | Herrin et al. |
| 5,733,628 | A | 3/1998 | Pelkie |
| 5,861,074 | A | 1/1999 | Wu |
| 5,921,973 | A | 7/1999 | Newkirk et al. |
| 6,072,005 | A | 6/2000 | Kobylivker et al. |
| 6,106,925 | A | 8/2000 | Palumbo |
| 6,210,386 | B1 | 4/2001 | Inoue |
| 6,476,289 | B1 | 11/2002 | Buell et al. |
| 6,540,731 | B2 | 4/2003 | Magnussson et al. |
| 6,552,245 | B1 | 4/2003 | Roessler et al. |
| 6,585,713 | B1 * | 7/2003 | LeMahieu et al. ........... 604/392 |
| 6,627,564 | B1 | 9/2003 | Morman et al. |
| 6,914,018 | B1 | 7/2005 | Uitenbroek et al. |
| 2002/0002021 | A1 | 1/2002 | May et al. |
| 2002/0052591 | A1 | 5/2002 | Zehner et al. |
| 2003/0022582 | A1 | 1/2003 | Cree et al. |
| 2003/0078558 | A1 | 4/2003 | Karami et al. |
| 2004/0078018 | A1 | 4/2004 | Van Gompel et al. |
| 2004/0102746 | A1 | 5/2004 | Mortell et al. |
| 2004/0116887 | A1 | 6/2004 | Thorson et al. |
| 2004/0122405 | A1 | 6/2004 | Van Gompel et al. |
| 2004/0122406 | A1 | 6/2004 | Moser et al. |
| 2004/0127878 | A1* | 7/2004 | Olson et al. ............ 604/385.16 |
| 2004/0192140 | A1 | 9/2004 | Schneider et al. |
| 2004/0197588 | A1 | 10/2004 | Thomas et al. |
| 2004/0241389 | A1 | 12/2004 | Chung et al. |
| 2004/0243086 | A1 | 12/2004 | Van Gompel et al. |
| 2005/0101216 | A1 | 5/2005 | Middlesworth et al. |
| 2005/0106980 | A1 | 5/2005 | Abed et al. |
| 2006/0148358 | A1 | 7/2006 | Hall et al. |
| 2008/0000003 | A1 | 1/2008 | Melander |
| 2008/0033387 | A1 | 2/2008 | Wastlund-Karlsson et al. |

FOREIGN PATENT DOCUMENTS

| | | | |
|---|---|---|---|
| EP | 0 302 957 | A2 | 3/1989 |
| EP | 0 360 929 | A1 | 4/1990 |
| EP | 0 409 307 | | 1/1991 |
| EP | 0 418 493 | | 3/1991 |
| EP | 0 486 006 | | 5/1992 |
| EP | 0 605 012 | | 7/1994 |
| EP | 0 861 647 | A2 | 9/1998 |
| EP | 0 714 351 | | 12/1998 |
| EP | 0 604 731 | B1 | 6/1999 |
| EP | 1 035 818 | | 9/2000 |
| EP | 1 184 022 | | 3/2002 |
| EP | 1 384 459 | A2 | 7/2003 |
| EP | 1 473 008 | | 11/2004 |
| FR | 2 586 558 | | 3/1987 |
| FR | 2 810 879 | | 1/2002 |
| GB | 2 284 538 | A | 6/1995 |
| JP | 06255006 | A | 9/1994 |
| JP | 07-252762 | | 10/1995 |
| JP | 9-286085 | | 11/1997 |
| JP | 10-043235 | A | 2/1998 |
| JP | 2002 058 703 | | 2/2002 |
| JP | 2002-065740 | | 3/2002 |
| JP | 2002-172137 | A | 6/2002 |
| JP | 2003-520146 | | 7/2003 |
| JP | 2003-290284 | | 10/2003 |
| JP | 2004-519270 | | 7/2004 |
| RU | 2 008 774 | C1 | 3/1994 |
| RU | 2 221 531 | | 1/2000 |
| SU | 965339 | | 10/1982 |
| TW | 233473 | | 11/1994 |
| WO | WO 95/19258 | | 7/1995 |
| WO | WO 96/10979 | A1 | 4/1996 |
| WO | WO 97/29722 | A1 | 8/1997 |
| WO | 97/34037 | | 9/1997 |
| WO | 98/37847 | | 9/1998 |
| WO | WO 99/27876 | A1 | 6/1999 |
| WO | WO 99/32164 | A1 | 7/1999 |
| WO | WO 00/02511 | A1 | 1/2000 |
| WO | WO 00/45764 | A1 | 8/2000 |
| WO | WO 01/30563 | A1 | 5/2001 |
| WO | WO 01/45927 | A1 | 6/2001 |
| WO | WO 01/53076 | | 7/2001 |
| WO | WO 02/34185 | | 5/2002 |
| WO | WO 02/49560 | A1 | 6/2002 |
| WO | WO 03/004748 | A1 | 1/2003 |
| WO | WO 03/019714 | A1 | 3/2003 |
| WO | 03/047488 | A1 | 6/2003 |
| WO | WO 2004/058120 | | 7/2004 |
| WO | WO 2004/060251 | A1 | 7/2004 |
| WO | WO 2004/078083 | A1 | 9/2004 |
| WO | WO 2005/122984 | A1 | 12/2005 |
| WO | WO 2005/122985 | A1 | 12/2005 |
| WO | WO 2006/038837 | A1 | 4/2006 |
| WO | WO 2006/093443 | A1 | 4/2006 |
| WO | WO 2006/093439 | A1 | 9/2006 |
| WO | WO 2006/093440 | A1 | 9/2006 |
| WO | WO 2007/114744 | A1 | 10/2007 |
| WO | WO 2008/060194 | A1 | 5/2008 |

OTHER PUBLICATIONS

Sueo Kawabata, "The Standardization and Analysis of Hand Evaluation", Second Edition, The Hand Evaluation and Standardization Committee, The Textile Machinery Society of Japan, published by The Textile Machinery Society of Japan, Osaka, Japan, Jul. 1980.

Wastlund-Karlsson et al., Copending U.S. Appl. No. 11/630,372, filed Dec. 21, 2006 entitled "Absorbent Article Comprising an Elastic Laminate".

Melander, Copending U.S. Appl. No. 11/845,153, filed Aug. 27, 2007 entitled "Underwear Article Comprising an Elastic Laminate".

Karlson et al., Copending U.S. Appl. No. 11/576,497, filed Dec. 3, 2008 entitled "Absorbent Article Comprising an Elastic Web Material".

Wennerback, Copending U.S. Appl. No. 12/446,297, filed Apr. 20, 2009 entitled "Absorbent Article Comprising an Elastic Laminate".

Norby et al., Copending U.S. Appl. No. 12/477,694, filed Apr. 29, 2009 entitled "Elastic Laminate and Absorbent Article Comprising the Laminate".

Wennerback, Copending U.S. Appl. No. 12/514,086, filed May 8, 2009 entitled "Absorbent Article Comprising an Elastic Laminate Material".

Non-Final Office Action in Copending U.S. Appl. No. 11/630,372 to Wastlund-Karlson et al. dated Sep. 16, 2009.

Final Office Action in Copending U.S. Appl. No. 11/630,372 to Wastlund-Karlson et al. dated Mar. 2, 2008.

Non-Final Office Action in Copending U.S. Appl. No. 11/630,372 to Wastlund-Karlson et al. dated Jul. 8, 2009.

An English Translation of the Notice of Reasons for Rejection issued in the corresponding Japanese Patent Application No. 2007-517994 dated Nov. 24, 2009.

* cited by examiner

ABSORBENT ARTICLE COMPRISING AN ELASTIC LAMINATE

FIELD OF THE INVENTION

The present invention refers to a pant type absorbent article such as a pant diaper, a sanitary pant or incontinence garment, said article having a core region comprising an absorbent core and a chassis region surrounding the core region, said chassis region comprising front, back and waist regions, while the core region is located at least in the crotch portion of the article, a liquid impermeable backsheet is arranged at least in the core region on the garment facing side of the absorbent core and a liquid permeable topsheet is arranged at least in the core region on the wearer facing side of the absorbent core.

BACKGROUND

Absorbent articles having defined core regions and chassis regions are supposed to have a comfortable fit about the wearer. For pant articles like pant diapers, sanitary pants and incontinence pants it is also desirable that the articles are capable of being pulled up and down over the hips of the wearer to allow the wearer or caregiver to easily put on and remove the article when it has been soiled. Furthermore, it is important that the absorbent article can be put on and taken off without breaking or puncturing, for instance by fingernails. It is known to make such absorbent pants with elasticized stretchable side panels and waist portion, usually comprising elastic members, such as elastic threads, contractably affixed between the backsheet and the topsheet.

It is further known to make portions of the chassis of absorbent articles of an elastic material, such as stretch-bonded laminates. Such laminates may include a layer of meltblown elastomeric fibers which have been stretched and sandwiched between outer layers of spunbonded webs.

U.S. Pat. No. 6,552,245 discloses an extensible outer cover for an absorbent article which provides a certain permanent deformation when subjected to a tensile force. The extensible outer cover comprises a necked laminate in the form of one layer of a necked non-elastic film and one layer of a non-elastic film. The films may be breathable.

WO 03/047488 discloses an elastic laminate comprising an elastic film which on opposite sides is bonded to first and second non-elastic fibrous layers. The laminate is made by bonding the non-elastic fibrous layers to the elastic film layer and subsequently stretching the composite material, causing the non-elastic materials to break. The elastic film material may be of a breathable material. The laminate may be incorporated in an absorbent article. No mention is made of the puncture resistance of such a material. The process described in WO 03/047488 will give a material which is soft and elastic, but which on the other hand has low resistance to puncturing, as the broken outer nonwoven layers will make no contribution to the puncture resistance of the laminate.

US2003/0022582 describes a laminate in which an elastomeric film is bound between two or more layers of nonwoven webs. The laminate is said to be particularly useful in elastic diaper "ears" that can be stretched to accommodate variously sized wearers. It is stated that nonwoven materials provide little or no puncture resistance, hence the any puncture resistance which the laminate has will be almost exclusively due to the puncture resistance of the elastomeric film.

Further examples of absorbent articles which in part are made of elastic laminates are found in U.S. Pat. No. 6,476,289 and JP 10043235.

There is however still room for improvement with respect to the strength of such laminates, particularly with respect to their resistance to puncture. The comfort, fit and cloth-like feel of absorbent articles of the above-mentioned type is also important.

SUMMARY AND OBJECTS

One of the objects of the present invention is to provide an absorbent article having a core region and a chassis region and which combines properties of comfort and fit to the wearer's body and a soft and cloth-like feeling close to textile materials. It is further desirable that the article can be put on and taken off without puncturing the same, e.g. by fingernails. This is an important feature, as the force which can be applied during putting on and taking off such an article has been estimated as being up to 5N. These and further objects have been accomplished by the fact that said article at least in part of the chassis region comprises a outer coversheet in the form of an elastic laminate having a puncture resistance of at least 15N, wherein the laminate is composed of first and second layers of fibrous material and an elastic film layer located between said first and second fibrous layers and in which at least one of the layers of fibrous material has an elongation at maximum load greater than the elasticity of the elastic laminate. Due to the materials and methods involved in its construction, the puncture resistance of this laminate is higher than the elastic film layer alone (i.e. the layers of fibrous material contribute to the puncture resistance of the laminate).

Preferably, the elastic laminate has a puncture resistance of at least 20N, more preferably at least 30N.

In one embodiment, both layers of fibrous material have an elongation at maximum load greater than the elasticity of the elastic laminate.

In a further embodiment, the elastic film layer is breathable.

In one aspect of the invention the elastic laminate has a Water Vapour Transmission Rate according to ASTM E96-00 Procedure D of at least 1500 g/m$^2$ 24 h, preferably at least 3000 g/m$^2$ 24 h.

According to a further aspect of the invention, the surface area of the absorbent core amounts to no more than 30%, preferably no more than 20% of the total surface area of the article, as measured in a flat state of the article.

According to a further embodiment, said elastic laminate has an elasticity in the transverse direction of the article of at least 30%, preferably at least 50%, more preferably at least 70%, when measured according to the elasticity test method specified in the description.

Characteristically, the layers of fibrous material have an elongation at maximum load of at least 10%, preferably at least 20% greater than the elasticity of the elastic laminate.

According to a further embodiment, a substantial part of the crotch portion of the article is free from said elastic laminate.

For certain applications it is preferred that the waist region of the chassis region is free from said elastic laminate.

In one aspect of the invention, said elastic laminate is arranged in at least a substantial part of the front region of the chassis, which in use is intended to be applied over the stomach of the wearer.

In one embodiment of the invention, the elastic laminate constitutes both the outer and the inner coversheet of the article in at least a part of the chassis region.

In yet a further embodiment, the first and/or the second layers of fibrous material comprise a mixture of polypropylene and polyethylene polymers.

In a further aspect of the invention, the article is a pull-up pant product comprising an elastic waist region, which is free from said elastic laminate, a crotch portion which is also free from said elastic laminate and wherein the elastic laminate is arranged in at least a substantial part of the front region of the chassis, which in use is intended to be applied over the stomach of the wearer.

According to one embodiment, said elastic laminate comprises first and second fibrous layers of spunbond material, each having a basis weight of between 10 and 35 g/m$^2$, preferably between 12 and 30 g/m$^2$, more preferably between 10 and 25 g/m$^2$, and a breathable elastic film layer having a basis weight between 20 and 100 g/m$^2$, preferably between 20 and 60 g/m$^2$, said elastic laminate having a Water Vapour Transmission Rate according to ASTM E96-00 Procedure D of at least 1500 g/m$^2$ 24 h, preferably at least 3000 g/g/m$^2$ 24 h.

BRIEF DESCRIPTION OF THE DRAWING FIGURES

DETAILED DESCRIPTION OF THE PREFERRED EMBODIMENTS

Figure 1:
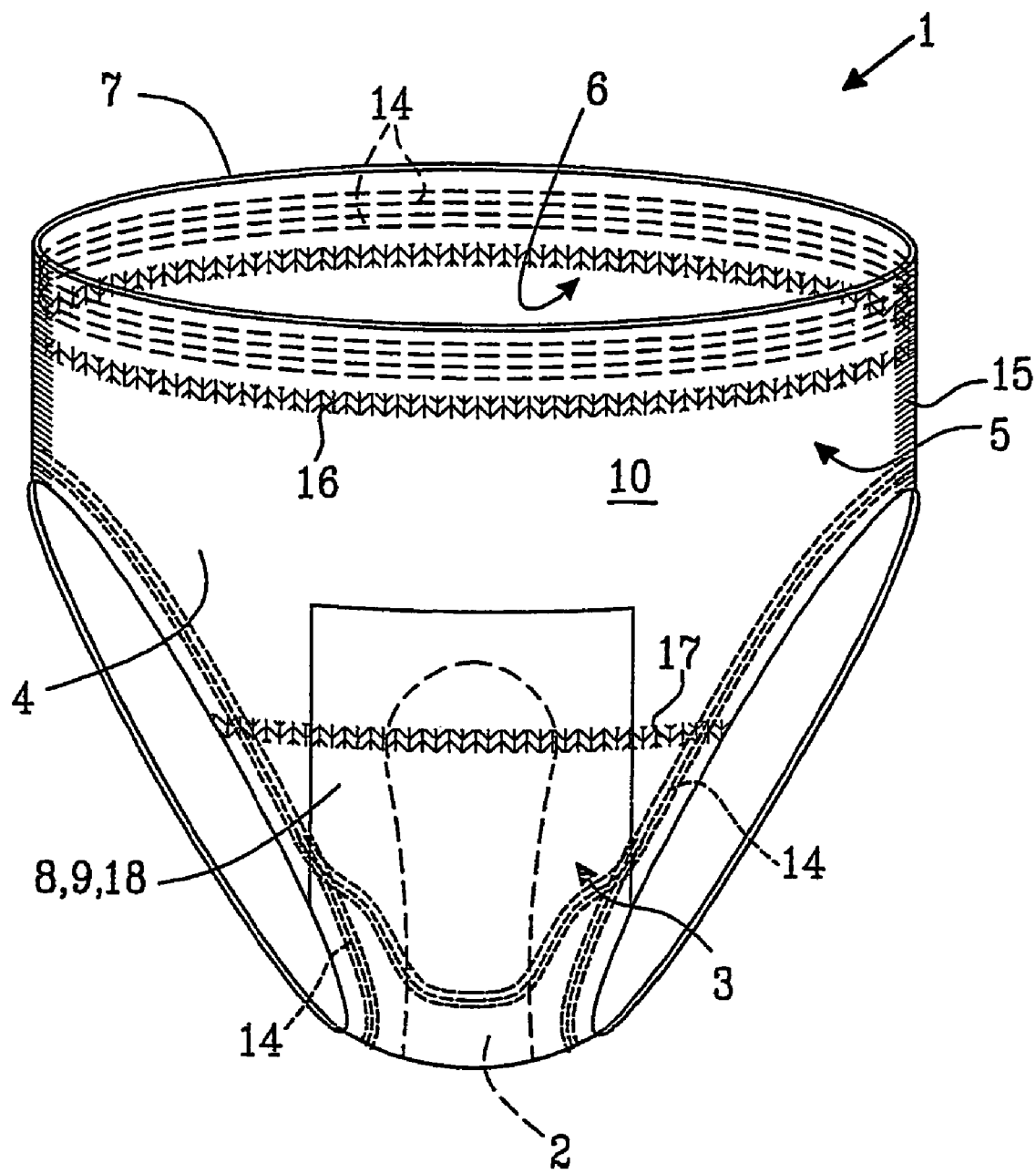
FIG. 1 shows a perspective view of a preferred embodiment of a pant diaper.

The invention is described in further detail below, with reference to the preferred embodiments shown in the accompanying drawings.

The term "absorbent article" refers to products that are placed against the skin of the wearer to absorb and contain body exudates, like urine, faeces and menstrual fluid. The preferred embodiments of the invention mainly refer to disposable absorbent articles, which means articles that are not intended to be laundered or otherwise restored or reused as an absorbent article after use. In addition, pant type absorbent articles are referred to having a core region and a chassis region surrounding the core region. Examples of such pant type absorbent articles are pant diapers, sanitary pants and incontinence pants.

The drawings show an embodiment of a pant diaper 1 for an infant or an incontinent adult. Said pant diaper typically comprises an absorbent core 2 located in a core region 3 of the article, and a chassis region 4 surrounding the core region. The chassis region comprises front 5, back 6 and waist regions 7. The core region 3 is located at least in the crotch portion (a) of the article and extends a certain distance into the front 5 and back regions 6. The crotch portion (a) is herewith defined as the narrow part of the article intended to be worn in the wearer's crotch between the legs. The article has a longitudinal direction y and a transverse direction x.

The article comprises a liquid permeable topsheet 8 and a liquid impermeable backsheet 9 covering the at least the core region 3. The absorbent core 2 is enclosed between the topsheet and the backsheet.

The liquid permeable topsheet 8 preferably includes a nonwoven material, e g spunbond, meltblown, carded, hydroentangled, wetlaid etc. Suitable nonwoven materials may comprise natural fibers, such as woodpulp or cotton fibres, manmade fibres, such as polyester, polyethylene, polypropylene, viscose etc. or a mixture of natural and manmade fibres. The topsheet material may further include tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. The topsheet may be different in different parts of the absorbent article.

The liquid impervious backsheet 9 covering the core region 3 on the garment-facing side of the core is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. The core region backsheet material 9 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet 9 is preferably inelastic.

The outer coversheet 10 covering the front and rear parts 5 and 6 of the chassis region 4 comprises an elastic laminate 11. The laminate is elastic at least in the transverse x-direction of the article. The elasticity in the x-direction should be at least 30%, preferably at least 50%, more preferably at least 70%, as measured by the elasticity test method specified below.

The elastic laminate 11 comprises first and second outer layers of fibrous material 12a and 12b and a middle elastic film layer 13 located between said fibrous layers. The outer fibrous layers 12a and 12b are chosen so that they, in combination with the inner elastic film layer, give the material high resistance to puncture. They also provide a soft and cloth-like feel to the laminate. Examples of suitable materials are carded webs and spunbond materials. The basis weight of the fibrous material layers should be preferably between 10 and 35 g/m$^2$, preferably between 12 and 30 g/m$^2$, more preferably between 15 and 25 g/m$^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

The middle layer is according to one embodiment of the invention an apertured elastic film having a basis weight preferably between 20 and 100 g/m$^2$, preferably between 20 and 60 g/m$^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The elastic laminate 11 may be manufactured according to a modified version of the method disclosed in WO 03/047488, wherein one spunbond layer 12a is applied to the film 13 in a tacky state and will thus bond to the film layer, while the other spunbond layer 12b is adhesively laminated to the film layer 13, using for example a pressure sensitive hot melt adhesive. The modification involves the laminate being incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break, that is, they are completely torn. Therefore, as described in WO 03/047488, the elongation of the laminate is not limited by the stretch modulus of the non-elastic material.

In contrast to the method described in WO 03/047488, upon manufacture of a laminate according to the present invention, at least one, preferably both fibrous layers which are bound to the elastic film are not completely torn. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably the fibrous layers, or at least one of the fibrous layers have an elongation at maximum load that is at least 10% higher than the elasticity of the laminate.

Figure 5:
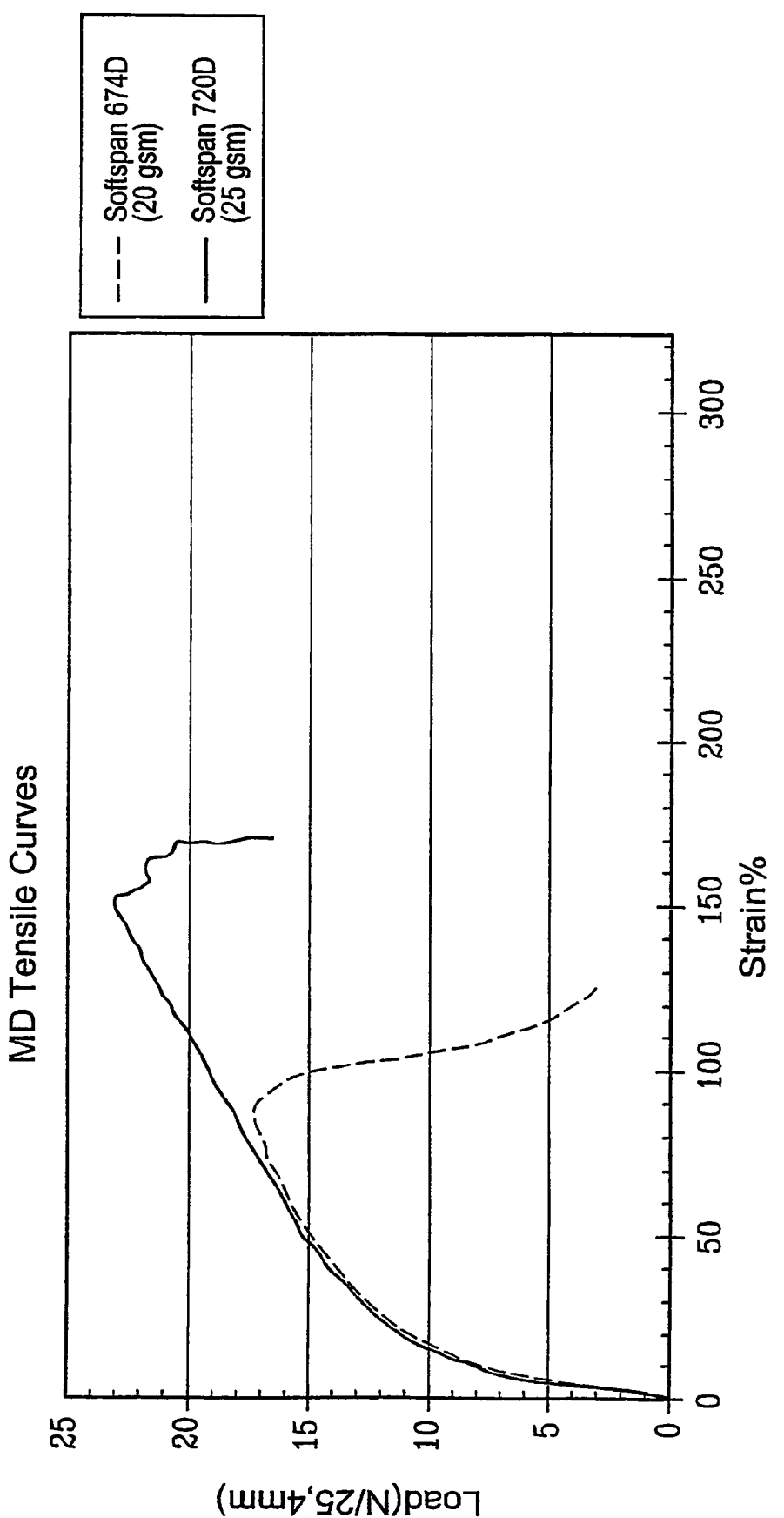
FIG. 5 is a graph showing load vs. strain for two nonwoven fibrous layers.

FIG. 5 shows the behaviour of two 20 gsm and 25 gsm nonwoven layers (BBA Sofspan 200) under stretching. It can be seen that, with increasing load (in Newtons), the strain in the layer increases, first slowly and then more rapidly. The applied load eventually reaches a maximum (the "maximum load"), at which point the load drops rapidly as the material fails. It can be seen that for the 20 gsm layer, maximum load is reached at around 90% strain, while for the 25 gsm layer, maximum load is reached at around 150% strain.

Figure 6:
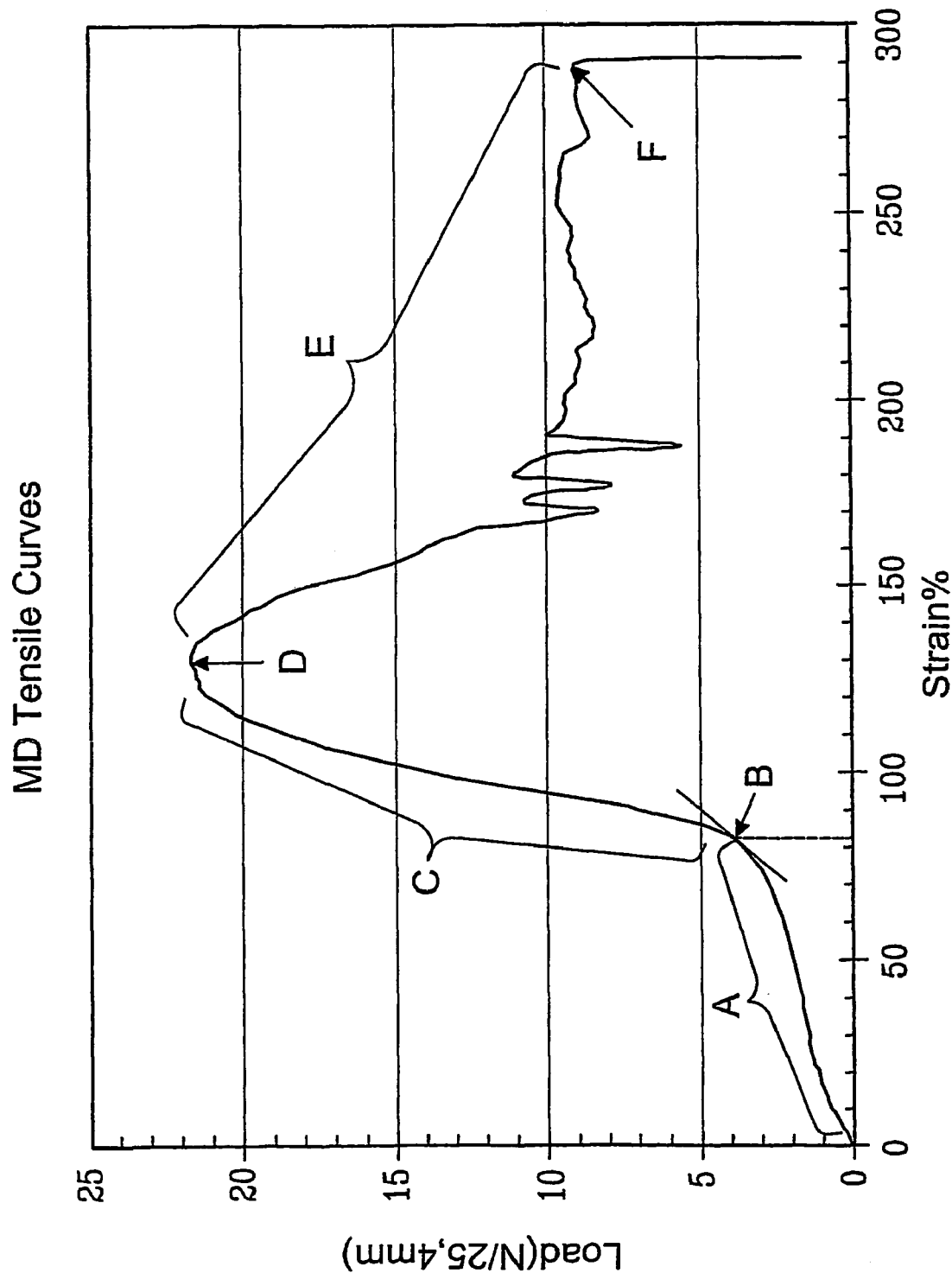
FIG. 6 is a graph showing load vs. strain for an elastic laminate.

FIG. 6 shows the behaviour of a laminate according to the present invention under stretching at a constant strain. The laminate comprises 25 gsm Sofspan NW from BBA on both sides of a 40 gsm apertured elastic film, where one face is glue-laminated with approximately 5 gsm glue.

From zero strain, the laminate exhibits elastic behaviour in region (A) up to around a "knee point" (B), after which, the load increases rapidly through region (C). The knee point (B) is defined as the first point on the load-strain curve at which the gradient becomes greater than 0.3N/%. The laminate shown is elastic up to about 80% strain—as this is less than the elongation (strain) at maximum load of the nonwoven layer (ca. 150% from FIG. 5), the laminate falls within the present invention.

The applied load eventually reaches a maximum (the "maximum load", D), at which point the gradient of the load-strain curve is zero. The load then drops through region (E) as the material fails. Complete failure of the laminate occurs at point (F).

It is preferred that the elastic laminate 11 has a breathability (Water Vapour Transmission Rate) according to ASTM E96-00 Procedure D of at least 1500 g/m$^2$ 24 h, preferably at least 3000 g/m$^2$ 24 h.

The absorbent core 2 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent. The size and absorbent capacity of the absorbent core may be varied to be suited for different uses such as for infants or for incontinent adults.

The pant diaper disclosed in FIG. 1 is intended to enclose the lower part of the wearer's trunk like a pair of absorbent pants. It comprises a core region 3 located in the narrow crotch portion of the article and extending into the front and back regions of the absorbent pants. A chassis region 4 surrounds the core region 3. The core region 3 is defined as the surface area of the article which is occupied by the absorbent core 2 and the areas outside the core which are covered by the liquid-impervious backsheet 9. The chassis region comprises front 5, back 6 and waist regions 7. The front 5 and back regions 6 are joined to each other along their longitudinal edges by ultrasonic welds 15, glue strings or the like.

Figure 2:
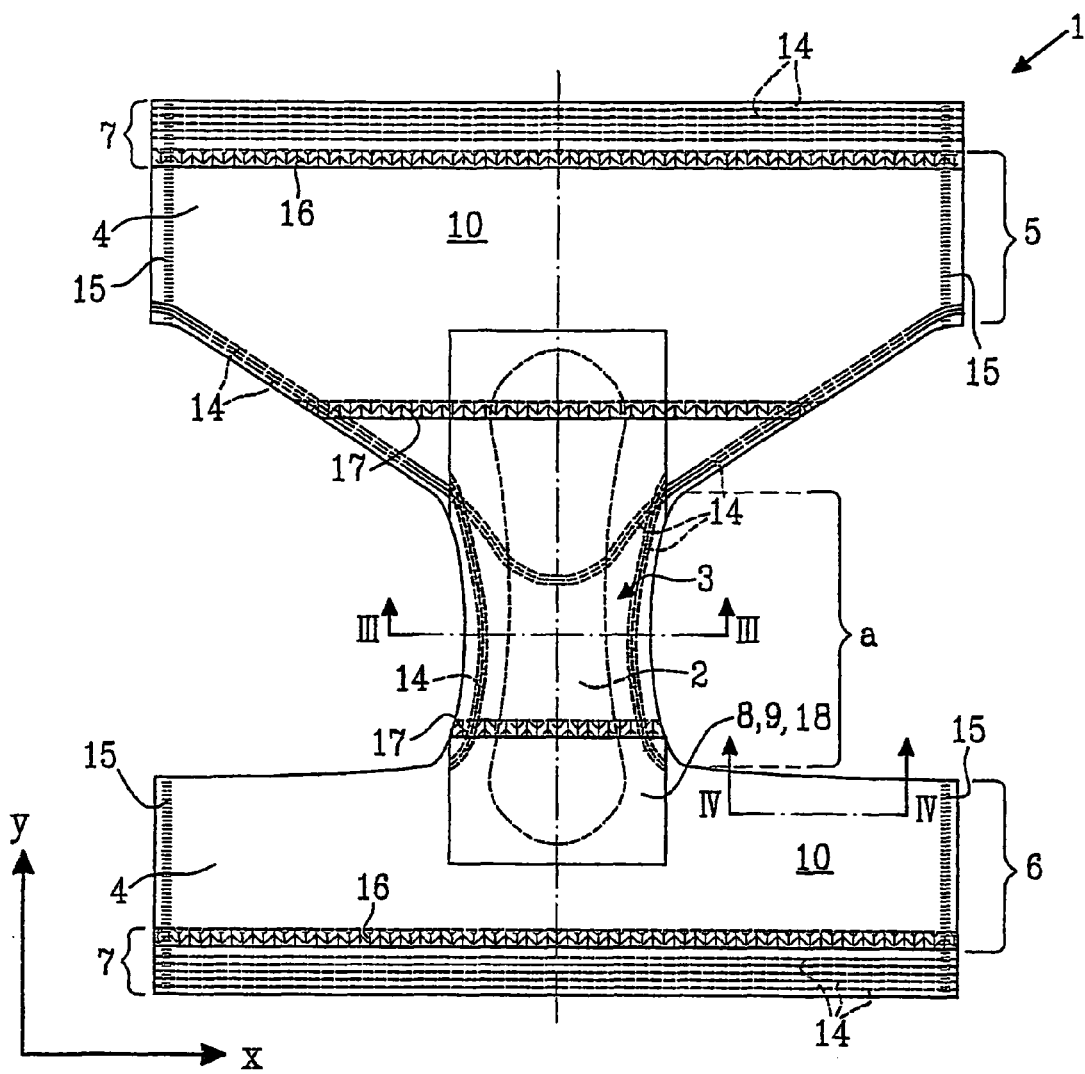
FIG. 2 shows is a simplified plan view of the pant diaper in its flat, uncontracted state prior to formation.
Figure 3:
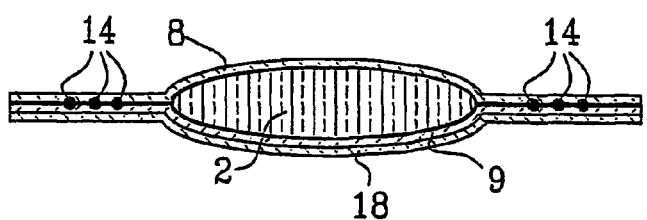
FIG. 3 is a cross section according to the line III-III in FIG. 2.
Figure 4:
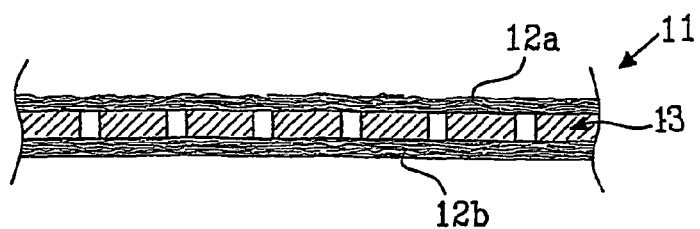
FIG. 4 is a cross section through an elastic laminate according to a preferred embodiment of the invention.

According to one embodiment of the invention the surface area of the absorbent core 2 amounts to no more than 30% of the total surface area of the article, preferably no more than 20%, as measured in a flat state of the article (see FIG. 2).

The elastic laminate 11 may cover the entire article, including the core region 3 and the entire chassis region 4. However according to a preferred embodiment a substantial part of the crotch portion of the article is free from the elastic laminate 11. A "substantial part" as used herein refers to at least 50%, preferably at least 75%. Preferably also the waist region 7 of the chassis region is free from the elastic laminate 11. The waist region 7 comprises a nonwoven material that is elasticized by elastic members 14, such as elastic threads, contractably affixed between material layers, such as nonwoven materials. Such elastic members 14 may also be arranged around the leg openings of the article. Ultrasonic welds 16, glue strings or the like, join the elastic laminate 11 to the elasticized nonwoven in the waist region 7.

The liquid-impervious backsheet material 9 underlies the absorbent core 2 and adjacent areas of the chassis region immediately outside the absorbent core 2. The area covered by the liquid-impervious backsheet 9 is defined as the core region 3. A nonwoven material 18 is arranged on the garment-facing side of the liquid-impervious backsheet 9 in the crotch portion of the article. The nonwoven material 18 is joined to the elastic laminate 11 by means of ultrasonic welds 17, glue strings or the like. The elastic laminate 11 and the liquid impervious backsheet overlap in the outer parts of the core region 3, as seen in FIG. 2, wherein the elastic laminate 11 is arranged on the garment facing side of the liquid impervious backsheet 9.

The elastic laminate 11 is preferably arranged as an outside coversheet material over a substantial part of the chassis region, except for the waist region 7. It is preferred that the elastic laminate is arranged at least over a substantial part of the front region 4 of the chassis region, which during use is intended to be applied against the stomach of the wearer. A "substantial part" used herein means at least 50% of the surface area, preferably at least 75% and most preferably at least 90% of the surface area of the front region 5 of the chassis. The elastic laminate 11 preferably also constitutes the inner coversheet of the article in said portions of the chassis region. Thus no additional topsheet material is required in these parts of the article.

No additional elasticized side panels joining the front and back regions 5 and 6 are needed when using the elastic laminate 11. If desired, additional elasticized side panels may of course be provided, especially in cases where the elastic laminate 11 is arranged only in parts of the front and/or back regions.

The elastic laminate should have a puncture resistance of at least 15N as measured according to ASTM Designation D3763-02. Preferably, the elastic laminate of the present invention has a puncture resistance of at least 20N, and more preferably at least 30N.

The elastic laminate should preferably have a softness according to Kawabata of at least 20, preferably at least 30 and most preferably at least 40.

It is further desired that it has a formability according to Kawabata of no more than 50, preferably no more than 30, more preferably no more than 20 and most preferably no more than 10.

It is also desired that the elastic laminate has a drapability according to Kawabata of no more than 40.

Description of Test Methods

Puncture Strength:

Puncture strength is measured according to ASTM Designation D3763-02. From penetration impact-type tests, this method produces data of load versus displacement. The maximum load for each laminate is calculated.

Tensile Strength: (Reference: ASTM D 882)

The method measures tensile strength and elongation of difference elastic materials. The tensile strength and elongation of a well-defined test piece is tested by means of a tensile tester.

Apparatus: Instron 4301
 Tensile tester connected to a computer
 Crosshead speed: 500 mm/min
 Clamp distance: 50 mm
 Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4 h in 50% RH±5% RH and 23° C.±2° C. before testing.

Procedure:

The tensile tester is calibrated according to the apparatus instructions and set to zero. The sample is mounted and it is ensured that it is not obliquely or unevenly fastened. The material is prevented from slipping by using clamps covered with galloon or similar material. The tensile tester is started, and stopped after the material has broken (if not automatically controlled). Measurements resulting from premature failures (i.e. the sample breaks at the clamp, or is damaged during preparation) are ignored if possible.

The following results are expressed by the tensile tester/computer:
 Maximum force, N/25.4 mm
 Elongation at maximum force, %
 Break force, N/25.4 mm
 Elongation at break force, %
 Knee point, N/%

Elasticity Test:

The Elasticity Test Method measures how an elastic material behaves at repeated load and unload cycles. According to the Elasticity Test Method, the sample is stretched to a predetermined elongation and a cyclic movement between 0 and said predetermined elongation is performed. Desired load and unload forces are recorded. The permanent, i.e. remaining, elongation of the relaxed material is measured.

A tensile tester, preferably a Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the specific apparatus instructions. The parameters needed for the test (load and unload forces) are adjusted to:
 Crosshead speed: 500 mm/min
 Clamp distance: 50 mm
 Preload: 0.05 N The sample is placed in the clamps according to the marks and it is made sure that the sample is centred and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus, using said Elasticity Test Method defined herein, an elasticity of 30% is characterized as the laminate preferably having a permanent relaxation after elongation of less than 10% after being exerted to an elongation of 30% in the tensile tester above. An elongation of 30% means an elongation to a length that is 30% longer than the initial length of the sample.

Kawabata Tests:

The Kawabata KES-FB test is a Japanese quality judgment system used for textile materials and is disclosed in "The Standardization and Analysis of Hand Evaluation (2nd Edition), Sueo Kawabata, July 1980, The Hand Evaluation and Standardization Committee, The Textile Machinery Society of Japan". The test used in the present invention preferably uses two of the Kawabata testing machines, KES-FB2 for measuring Bending rigidity, B (gf·cm$^2$/cm), and KES-FB1 for measuring Shear stiffness, G (gf/cm·degree) and Tensile strain, EMT (%).

Bending Rigidity (B) KES-FB2
 The slope was measured between 0.5 cm$^{-1}$ and 1.5 cm$^{-1}$ and −0.5 cm$^{-1}$ and −1.5 cm$^{-1}$.
 The measurements were performed in both directions (MD and CD) with the following settings:
 Total sample area: 20×20 cm;
 Maximum curvature: Kmax=±2.5 cm$^{-1}$;
 Bending rate: 0.5 cm$^{-1}$/sec;
 Sample effective dimension: 20 cm length and 1 cm width;
 Bending deformation is applied to the width direction.

Shear Stiffness (G) KES-FB1
 The slope was measured between 0.5 cm$^{-1}$ and 2.5 cm$^{-1}$ and −0.5 cm$^{-1}$ and −2.5 cm$^{-1}$.
 The measurements were performed in both directions (machine direction, MD, and cross direction, CD) with the following settings:
 Total sample area: 20×20 cm;
 Tension of specimen: W=W=10 gf/cm;
 Maximum shear angle: φ=±8°.

Sample effective dimension: 20 cm width and 5 cm length;
Shear deformation is applied to the width direction.

Tensile Strain (EMT)

The measurements were performed in both directions (machine direction, MD and cross direction, CD) with the following settings:
Total sample area: 20×20 cm;
Maximum load: Fm=500 gf/cm;
Tensile speed: 0.2 mm/sec.
Sample effective dimension: 20 cm width and 2.5 cm length;
Tensile deformation is applied to the length direction.
Elongation sens 50 mm/10V.

Softness (S)

The Softness (S) according to Kawabata is obtained from the formula:

$$S = \sqrt{EMT/B}$$

Formability (F)

The Formability (F) according to Kawabata is obtained from the formula:

$$F = B \cdot EMT$$

Drapability (D)

The Drapability (D) according to Kawabata is obtained from the formula: $D=116+25 \cdot \log(B \cdot G/W)$, wherein W is the basis weight of the sample.

EXAMPLES

Puncture Resistance

The puncture resistance of three different samples (A, B and C) were measured according to ASTM Designation D3763-02 and are shown in Table 1.

Tensile Strength

The puncture resistance of three different samples (A, B and C) were measured according to the method given above and are shown in Table 1.

Elasticity

The elasticity of three different samples (A, B and C) were measured according to the Elasticity Test Method given above and are shown in Table 1.

Sample A is an elastic laminate according to WO03/047488 with 15 gsm PP spunbond nonwoven on both sides of a 40 gsm elastic film. The used spunbond nonwoven has an elongation at maximum load of 60%, which is less than the elasticity of the laminate. The low puncture resistance of this material means that it falls outside the scope of the present invention.

Sample B is an elastic laminate with 25 gsm PP/PE spunbond nonwoven on both sides of a 36 gsm elastic film.

Sample C is an elastic laminate with one layer of 25 gsm PP/PE nonwoven and one layer of 20 gsm PP/PE nonwoven on opposite sides of a 36 gsm elastic film.

TABLE 1

|  | Sample A | Sample B | Sample C |
|---|---|---|---|
| Puncture force (N) | 12.8 | 49.5 | 40.6 |
| Basis weight (gsm) | 78.66 | 87.96 | 82.71 |
| Tensile strength and Elongation MD (machine direction) | | | |
| Tensile strength at Peak (MD), N/25 mm | 8.29 | 25.3 | 28.03 |
| Elongation at break, % | 269.82 | 311.94 | 691.47 |
| Elongation at Peak/Deformation, % | 136 | 111.44 | 109.28 |
| CD (cross direction) | | | |
| Tensile strength at Peak (CD), N/25 mm | 11.72 | 11.15 | 9.16 |
| Elongation at break, % | 792.87 | 768.19 | 160.15 |
| Elongation at Peak/Deformation, % | 74.88 | 124.82 | 134.42 |
| Determination of load & unload forces and permanent elongation | | | |
| Tensile strength at 80% elongation (1$^{st}$ cycle) | 2.78 | 7.11 | 10.66 |
| Permanent Elongation (3$^{rd}$ cycle) | 7.86 | 7.52 | 8.09 |
| 3$^{rd}$ Retraction Forces | | | |
| At 80%, N/25 mm | 1.14 | 1.44 | 1.42 |
| At 60%, N/25 mm | 0.82 | 0.85 | 0.8 |
| At 40%, N/25 mm | 0.54 | 0.53 | 0.48 |

Kawabata Tests

Four different samples were measured in a Kawabata test with respect to Bending rigidity (B), Shear stiffness (G) and Tensile strain (EMT). From these measured values the Softness (S), Formability (F) and Drapability (D) were calculated.

The four samples were:

Sample laminate (SL): an elastomeric laminate according to the invention comprising an inner apertured three-layer elastomeric film of PE-SEBS-PE, basis weight 36 g/m$^2$ and two outer layers of spunbond material, PP (polypropylene), each having a basis weight of 22 g/m$^2$. The laminate is produced by a modified version of the method disclosed in WO 03/04788 and which is described above, wherein one spunbond layer is applied to the film in a tacky state and will thus bond to the film layer, while the other spunbond layer is adhesively laminated to the film layer using for example a pressure sensitive hot melt adhesive (glue amount 3 g/m$^2$). The laminate is incrementally stretched, at which the non-elastic spunbond layers are stretched to a point below the elongation at maximum load to retain some strength in the spunbond layers. The elasticity of the laminate after stretching is close to the elasticity of the elastomeric film layer.

The above-mentioned basis weights of the layers refer to the finished laminate after stretching. Before stretching the basis weight of the individual layers were: inner film layer 40 g/m$^2$, outer spunbond layers 25 g/m$^2$ each and glue layer 3 g/m$^2$. Since it is difficult to measure the basis weights of the individual layers after lamination and stretching an approximation has been made from the basis weights of the layers before lamination and stretching. The laminate before stretching had a total basis weight before stretching of 93 g/m$^2$ and after stretching it had a basis weight of 85 g/m$^2$, which means a deformation of about 10%. It is then assumed that the deformation of the individual fibrous layers and the film layer is the same, i.e. about 10%.

Ref. 1: Cotton-knitted goods, so called jersey with elastomeric threads.

Ref. 2: Outer coversheet of Tena Discreet incontinence pant (odour control, size medium) produced by SCA Hygiene Products AB. The outer coversheet comprises two layers of nonwoven with parallel elastic threads there between, which wrinkle the material.

Ref. 3: Outer coversheet material of Poïse normal super incontinence pant produced by Kimberly-Clark. The outer coversheet comprises two layers of nonwoven with parallel elastic threads there between which wrinkle the material.

A climate conditioning of the materials were performed at 20° C. and 65% RH for 48 hours. For the pant products, the absorbent core was removed and the outer coversheet was stretched over a knitwear measuring device for 24 hours and was then allowed to relax in the same climate during 24 hours.

The sizes of the samples were 10×10 cm.

All tests were made on three samples and in two material directions (machine direction, MD, and cross direction, CD).

The following results were obtained.

TABLE 2

| Sample | B, Bending rigidity (gf·cm²/cm) | | | G, Shear stiffness (gf/cm·degree) | | | EMT, Tensile strain (%) | | |
|---|---|---|---|---|---|---|---|---|---|
| | MD | CD | Mean | MD | CD | Mean | MD | CD | Mean |
| SL | 0.095 | 0.022 | 0.059 | 1.46 | 1.38 | 1.42 | 208.4 | 92.0 | 150.2 |
| Ref. 1 | 0.03 | 0.03 | 0.03 | 0.58 | 0.64 | 0.61 | 160.6 | 173.2 | 166.9 |
| Ref. 2 | 1.05 | 0.09 | 0.57 | 0.87 | 0.68 | 0.77 | 23.9 | 211.7 | 117.8 |
| Ref. 3 | 1.53 | 0.04 | 0.78 | 1.74 | 1.21 | 1.47 | 26.28 | 195.3 | 110.8 |

From these results the Softness (S), the Drapability (D) and the Formability (F) according to Kawabata were calculated according to the formulas stated above. These results are stated in Table 3 below.

TABLE 3

| Sample | Softness (S) Error! Objects cannot be created from editing field codes. | Drapability (D) 116 + 25 log(B·G/W) | Formability (F) B·EMT | Basis Weight (W) g/m² |
|---|---|---|---|---|
| SL | 50 | 40 | 9 | 88 |
| Ref. 1 | 75 | 13 | 5 | 231 |
| Ref. 2 | 14 | 45 | 67 | 160 |
| Ref. 3 | 12 | 51 | 87 | 133 |

The results should be interpreted in the following way:
Softness (S): a higher value indicates a softer material.
Drapability (D): a higher value indicates a stiffer material.
Formability (F): a higher value indicates that the material is less formable.

The test laminate according to the preferred invention has a Softness (S) and a Formability (F) according to Kawabata which is close to cotton-knitted goods (Ref. 1). Also the Drapability (D) according to Kawabata is closer to the cotton-knitted reference material than the other two tested materials, used as outer coversheets on conventional incontinence pants. Thus the use of the elastomeric laminate as outer coversheet material in at least a part of the chassis region of the absorbent pant provides a pant article having a cloth-like feeling close to a cotton material. The pant will also have an excellent comfort and fit to the wearer's body. By using the elastomeric laminate only in those parts of the pant in which the properties of the material is best utilized, a very economic utilization of the material is accomplished.

It is preferred that the laminate has a Softness (S) according to Kawabata of at least 20, more preferably at least 30 and most preferably at least 40. It is also preferred that the laminate has a Formability (F) according to Kawabata of no more than 50, preferably no more than 30, more preferably no more than 20 and most preferably no more than 10. It is also preferred that the laminate has a Drapability (D) according to Kawabata of no more than 40.

The invention claimed is:

1. A pant type absorbent article, said article having a core region comprising an absorbent core and a chassis region surrounding the core region, said chassis region comprising front, back and waist regions, while the core region is located at least in a crotch portion of the article, a liquid impermeable backsheet is arranged at least in the core region on the garment-facing side of the absorbent core and a liquid permeable topsheet is arranged at least in the core region on the wearer-facing side of the absorbent core, said article having a longitudinal and a transverse direction, wherein said article, at least in part of the chassis region, comprises an outer coversheet in the form of an elastic laminate having a puncture resistance of at least 15N,
wherein the laminate is composed of first and second layers of fibrous material and an elastic film layer located between said first and second fibrous layers and in which at least one of the layers of fibrous material has an elongation at maximum load greater than the elasticity of the elastic laminate.

2. The absorbent article as claimed in claim 1, wherein said elastic laminate has a puncture resistance of at least 20N.

3. The absorbent article as claimed claim 1, wherein both layers of fibrous material have an elongation at maximum load greater than the elasticity of the elastic laminate.

4. The absorbent article as claimed in claim 1, wherein said elastic film layer is breathable.

5. The absorbent article as claimed in claim 4, wherein said elastic laminate has a Water Vapour Transmission Rate according to ASTM E96-00 Procedure D of at least 1500 g/g/m² 24 h.

6. The absorbent article as claimed in claim 1, wherein said elastic laminate has an elasticity in the transverse direction of the article of at least 30%, when measured according to the defined Elasticity Test Method.

7. The absorbent article as claimed in claim 6, wherein the layers of fibrous material have an elongation at maximum load of at least 10% greater than the elasticity of the elastic laminate.

8. The absorbent article as claimed in claim 7, wherein the layers of fibrous material have an elongation at maximum load of at least 20% greater than the elasticity of the elastic laminate.

9. The absorbent article as claimed in claim 6, wherein said elastic laminate has an elasticity in the transverse direction of the article of at least 70%.

10. The absorbent article as claimed in claim 1, wherein a substantial part of the crotch portion of the article is free from said elastic laminate.

11. The absorbent article as claimed in claim 10, wherein the waist region of the chassis region is free from said elastic laminate.

12. The absorbent article as claimed in claim 10, wherein said elastic laminate is arranged in at least a substantial part of the front region of the chassis, which in use is intended to be applied over the stomach of the wearer.

13. The absorbent article as claimed in claim 1, wherein the surface area of the absorbent core amounts to no more than 30% of the total surface area of the article, as measured in a flat state of the article.

14. The absorbent article as claimed in claim 1, wherein the first and/or the second layers of fibrous material comprise a mixture of polypropylene and polyethylene polymers.

15. The absorbent article as claimed in claim 1, wherein the article is a pull-up pant product comprising an elasticized waist region, which is free from said elastic laminate, a crotch portion which is also free from said elastic laminate and wherein the elastic laminate is arranged in at least a substantial part of the front region of the chassis, which in use is intended to be applied over the stomach of the wearer.

16. The absorbent article as claimed in claim 1, wherein said first and second fibrous layers comprise a spunbond material, each layer having a basis weight of between 10 and 35 g/m² and said elastic film layer comprises a breathable elastic film layer having a basis weight between 20 and 100 g/m², said elastic laminate having a Water Vapour Transmission Rate according to ASTM E96-00 Procedure D of at least 1500 g/m² 24 h.

17. The absorbent article as claimed in claim 1, wherein the article is a pant diaper, a sanitary pant or an incontinence pant.

18. The absorbent article as claimed in claim 5, wherein said elastic laminate has a Water Vapour Transmission Rate of at least 3000 g/g/m² 24 h.

19. The absorbent article as claimed in claim 1, wherein the elastic laminate has a puncture resistance of at least 30N.

20. The absorbent article as claimed in claim 6, wherein said elastic laminate has an elasticity in the transverse direction of the article of at least 50%.

21. The absorbent article as claimed in claim 1, wherein said first and second fibrous layers comprise a spunbond material, each layer having a basis weight of between 12 and 30 g/m² and said elastic film layer comprises a breathable elastic film layer having a basis weight between 20 and 60 g/m², said elastic laminate having a Water Vapour Transmission Rate according to ASTM E96-00 Procedure D of at least 3000 g/g/m² 24 h.

22. The absorbent article as claimed in claim 21, wherein said first and second fibrous layers of spunbond material each have a basis weight of between 15 and 25 g/m².

23. A pant type absorbent article, said article having a core region comprising an absorbent core and a chassis region surrounding the core region, said chassis region comprising front, back and waist regions, while the core region is located at least in a crotch portion of the article, a liquid impermeable backsheet is arranged at least in the core region on the garment-facing side of the absorbent core and a liquid permeable topsheet is arranged at least in the core region on the wearer-facing side of the absorbent core, said article having a longitudinal and a transverse direction, wherein said article, at least in part of the chassis region, comprises an outer coversheet in the form of an elastic laminate having a puncture resistance of at least 15N, wherein the laminate is composed of first and second layers of fibrous material and an elastic film layer located between said first and second fibrous layers, wherein the laminate is incrementally stretched above the point of failure of at least one of the fibrous layers so that the fibers in the layer are torn but to a point below elongation at peak load of at least one of the layers of fibrous material, and at least one of the layers of fibrous material has an elongation at maximum load greater than the elasticity of the elastic laminate.

24. A pant type absorbent article, said article having a core region comprising an absorbent core and a chassis region surrounding the core region, said chassis region comprising front, back and waist regions, while the core region is located at least in a crotch portion of the article, a liquid impermeable backsheet is arranged at least in the core region on the garment-facing side of the absorbent core and a liquid permeable topsheet is arranged at least in the core region on the wearer-facing side of the absorbent core, said article having a longitudinal and a transverse direction, wherein said article, at least in part of the chassis region, comprises an outer coversheet in the form of an elastic laminate having a puncture resistance of at least 15N, wherein the laminate is composed of first and second layers of fibrous material and an elastic film layer located between said first and second fibrous layers, wherein the first fibrous layer is applied to the elastic film layer in a tacky state and the second fibrous layer is adhesively laminated to the elastic film layer, and the laminate is incrementally stretched to a point below elongation at peak load of at least one of the layers of fibrous material, and at least one of the layers of fibrous material has an elongation at maximum load greater than the elasticity of the elastic laminate.

\* \* \* \* \*